(12) United States Patent
Tiffany et al.

(10) Patent No.: US 6,565,861 B1
(45) Date of Patent: May 20, 2003

(54) ARTIFICIAL TEAR FORMULATION

(75) Inventors: John Michael Tiffany, Headington (GB); Beatrix Valeria Macey-Dare, Oxford (GB)

(73) Assignee: ISIS Innovation Limited (GB)

( * ) Notice: Subject to any disclaimer, the term of this patent is extended or adjusted under 35 U.S.C. 154(b) by 0 days.

(21) Appl. No.: 09/774,217

(22) Filed: Jan. 30, 2001

Related U.S. Application Data

(63) Continuation of application No. 09/885,260, filed on Feb. 11, 2000.
(60) Provisional application No. 60/181,890, filed on Feb. 11, 2000.

(51) Int. Cl.[7] .............................. A61K 9/00; A61K 9/08; A61K 9/14
(52) U.S. Cl. ..................... 424/400; 424/401; 424/489; 424/490
(58) Field of Search ................................ 424/400, 401, 424/489, 490

(56) References Cited

U.S. PATENT DOCUMENTS

| | | | | |
|---|---|---|---|---|
| 5,306,483 A | * | 4/1994 | Mautone | 424/45 |
| 6,194,457 B1 | * | 2/2001 | Braswell et al. | 514/547 |

FOREIGN PATENT DOCUMENTS

| | | |
|---|---|---|
| FR | 2627386 A | 8/1989 |
| WO | WO 91/12808 A1 | 9/1991 |
| WO | WO 95/29696 A1 | 11/1995 |
| WO | WO 99/06022 A1 | 2/1999 |

OTHER PUBLICATIONS

B. Glasgow et al. Tear Lipocalins: Potential Lipid Savengers for the Corneal Surface. Investigative Ophthalmology & Visual Science, Dec. 1999, vol. 40, No. 13 pp. 3100–3107.*
Bishop, R.E. et al. "'Outlier' lipocalins more than peripheral" *TIBS* 21(4):127 (Apr. 1996).
Glasgow, B. et al. "Tear lipocalins bind a brad array of lipid ligands" *Current Eye Research* 14:363–372 (1995).

* cited by examiner

*Primary Examiner*—Thurman K. Page
*Assistant Examiner*—Rachel M. Bennett
(74) *Attorney, Agent, or Firm*—Lahive & Cockfield LLP; Anthony A. Laurentano; Peter C. Lauro

(57) ABSTRACT

Provided by the present invention are formulations suitable for application to mammalian eyes which contain a lipid binding protein and a polar lipid, present as a soluble complex in an aqueous electrolyte. The formulations described have shear-thinning (non-Newtonian viscosity) and surface tension properties to natural tears and are therefore useful as artificial tear substitutes for the treatment of dry eyes (e.g. keratoconjunctivitis sicca) and useful in ophthalmic applications in general.

17 Claims, 2 Drawing Sheets

Whole tears

Tears without lipids

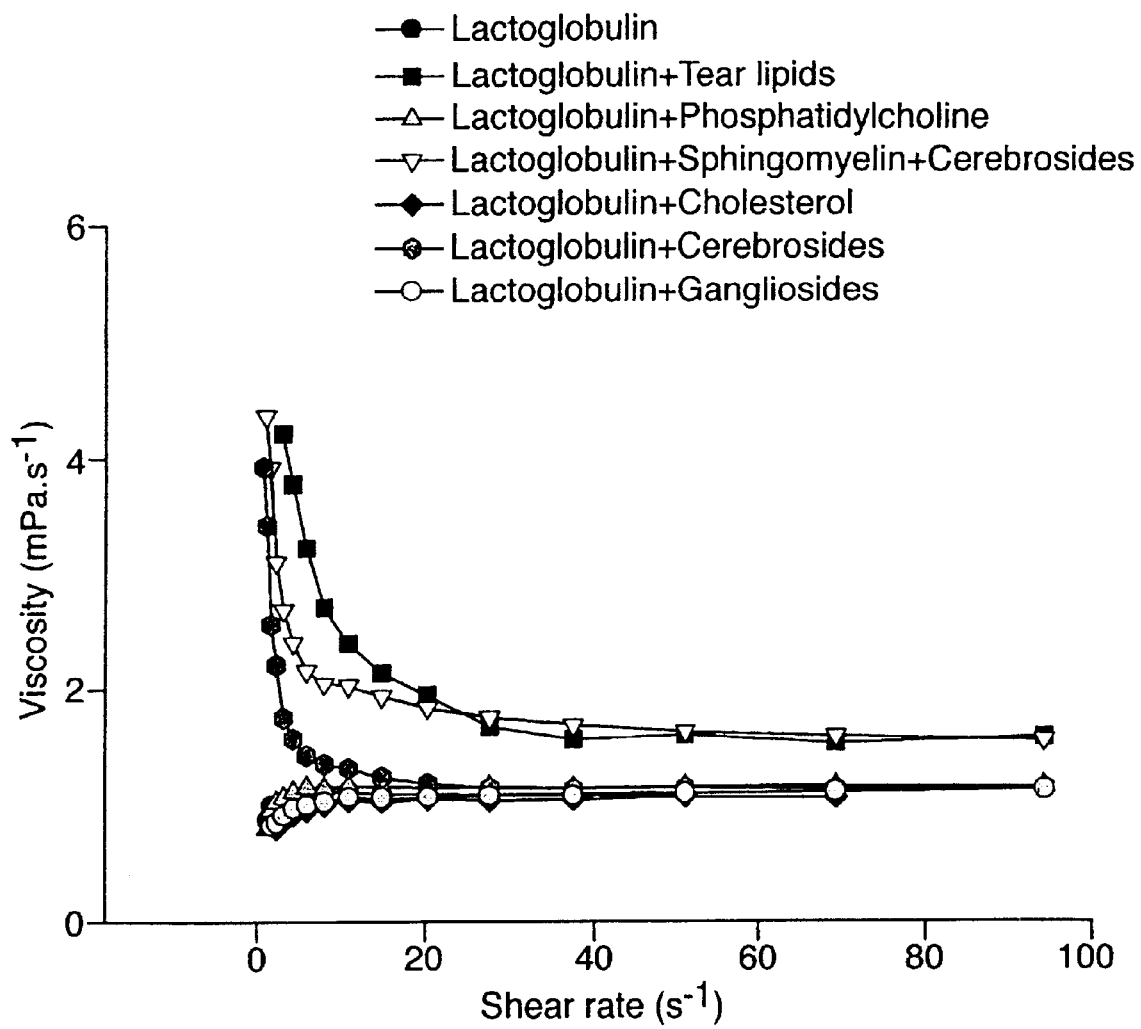

ARTIFICIAL TEAR FORMULATION

Figure 1A:
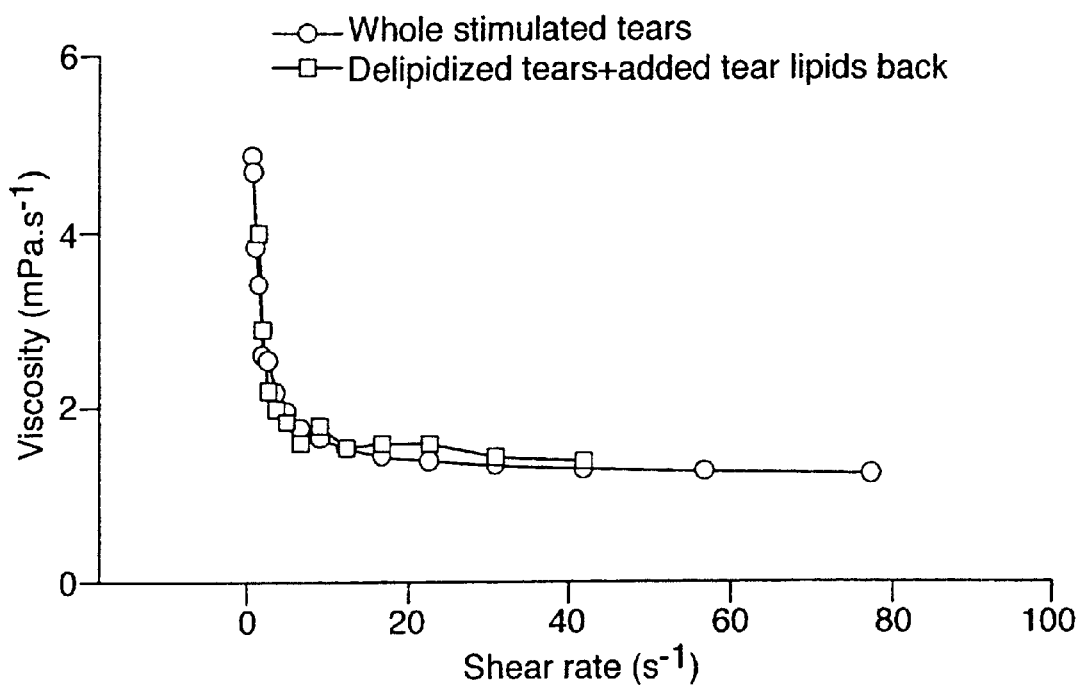

This application is a continuation of U.S. application Ser. No. 09/885,260, filed Feb. 11, 2000, which was originally filed as provisional application Ser. No. 60/181,890, filed Feb. 11, 2000.

INTRODUCTION

Human tears are composed of water, electrolytes, small molecules such as carbohydrates and lipids, and a variety of proteins, several of which have an enzymic function. The principal proteins of tears include lysozyme (an enzyme which attacks bacterial cell walls), lactoferrin (an iron-sequestering and thus bacteriostatic protein with a free-radical scavenging function), secretory IgA antibodies, and lipid binding proteins of the lipocalin family (previously known as tear-specific prealbumin). A wide variety of other enzymes (e.g. glycosidases and lysosomal hydrolases) is also present but in much smaller amounts.

Present formulations of artificial tears act by replacing the volume of the tear film, but they can only do this while they remain in contact with the surface of the eye. A simple saline solution would remain in contact with the eye surface for only a few seconds and thus a viscosity improving component is required in the formulation. Such components presently used include hypromellose, hydroxyethylcellulose, carboxymethylcellulose, polyvinyl pyrrolidone, polyvinyl alcohol, polyethylene glycol, dextran, hyaluronic acid, or carbomer 940 (polyacrylic acid). Such compounds act by mimicking the mucus present on the corneal surface and may interact with such mucus already present.

The presence of such mucus mimicking (mucomimetic) components can, in some instances, lead to symptoms of blurred vision due to slow mixing with tears, and irritation caused by the crystallisation of said components on lids and lashes.

Certain properties of natural human tears need to be understood for the better formulation of artificial tears to be used in treatment or alleviation of "dry eye" symptoms. Dry eye is a disorder of the tear film due to tear deficiency or excessive tear evaporation which causes damage to the exposed surface of the eye and is associated with symptoms of eye discomfort. Key physical properties involved in the function of fluid tears are surface tension and viscosity, both of which are thought to be important in spreading and maintenance of the pre-ocular tear film. Since dry eyes may be deficient in components which modulate these properties, any artificial tear formulation should contain these or suitable model materials having the same effect.

The viscosity of tears is shear-dependent and shows shear-thinning—i.e. the viscosity is high if measured at low speeds, but falls as the speed increases, and at high speeds (shear rates) approaches that of the solvent (Tiffany, 1991). This has advantages in the eye, in resisting gravitational drainage at low shears (eye open) but avoiding viscous dragging and epithelial damage at high shears (blinking).

It was thought at one time that mucus dissolved in the tears was, because of its known effect on viscosity and surface tension in mucus solutions, also responsible for these physical properties in tears. Having discovered that there is in fact little or no mucus in tears (Tiffany et al., 1996), or too little to have the observed effect, the inventors investigated other possible agents among the known constituents of human tears. It seemed possible that a small molecule such as a lipid might be responsible.

The vast majority of tear-associated lipid, such as that found bound to mucus collected from the eye (Moore and Tiffany, 1979) is from the Meibomian glands of the eyelid margin. Meibomian lipid is brought into contact with the aqueous fluid in formation of the pre-ocular film, but Stuchell et al. (1984) had reported a variety of polar lipids in tears, quite independent of this and of unknown tissue origin.

Of the known macromolecular components of tears, only a lipocalin protein, previously known as tear-specific prealbumin, is known to have any lipid-binding capacity, and has a broad lipid class specificity (Glasgow et al. 1995). Tear lipocalin is one member of a broad family of lipid-binding proteins called the lipocalins; many of these are small molecules (ca. 18–20 kDa) and include retinol-binding protein in serum and β-lactoglobulin in bovine milk (Flower, 1996). The inventors surmised that extractable lipids might therefore be bound to tear lipocalin in such a way as to influence surface tension, but that other lipids might produce the same effect if all that is necessary is a protein-lipid interaction.

THE INVENTION

Thus the invention provides in one aspect, a formulation suitable for application to mammalian eyes, which formulation comprises a pharmaceutically acceptable, substantially isotonic aqueous electrolyte buffered at a pH of 5 to 8.5, containing a lipid binding protein such as tear lipocalin at a concentration of from 0.01 to 50 mg/ml, and a polar lipid selected from phospholipids and glycolipids, at a concentration of from 1 µg/ml to 10 mg/ml.

In a preferred embodiment the lipid(s) and lipid binding protein are present as a soluble complex in the aqueous electrolyte. In a further embodiment, the formulation also contains one or more pharmaceutically acceptable preservative or bacteriostatic compounds, such as benzalkonium chloride, disodium EDTA or sodium perborate.

In a more preferred embodiment, the formulation, containing a lipid protein complex and suitable preservatives, shows shear-thinning and/or a surface tension of less than 47 mN/m.

A preferred range of cations for use in the aqueous electrolyte would be any of Na, K, Ca, or Mg. A preferred range of anions would be any of Cl or $HCO_3$, bearing in mind the preference for full solubility of the salt used.

The formulation should preferably be isotonic, or slightly hypotonic in order to combat any hypertonicity of tears caused by evaporation and/or disease. A preferable osmotic pressure for the solution would be 200–500 mOsmol/kg Preferred protein choice(s) for inclusion in the formulation would be from any of lysozyme, lactoferrin, IgA, β-lactoglobulin or lipocalin, or any other protein, preferably lipid-binding, capable of reducing the surface tension and facilitating shear-thinning when present in the formulation, described above. Optionally recombinant human tear-specific prealbumin would be used. This could be produced by methods well known in the art using the cloned gene for human tear lipocalin (Lassagne & Gachon, 1993). A process for the production of human lysozyme from a synthetic gene is disclosed in EP0181634. A preferable range of protein concentration in the formulation would be 0.9 to 1.7 mg/ml.

The use of proteins from other species or manufactured using recombinant techniques in a formulation as above, raises the possibility of toxic, allergenic and/or immunogenic effects. Therefore, the formulation of the invention would preferably contain a non-toxic, non-immunogenic, hypoallergenic protein as the protein component.

Preferred choice(s) of lipid component(s) would be any polar member(s) of any of the phospholipid, glycolipid and sphingolipid classes capable of reducing the surface tension and facilitating shear-thinning when present in the formulation as previously described. Such classes of lipid include the sphingosides, ceramides and gangliosides, and others as described in Gunstone and Herslöf, (1992). The lipid may have limited solubility. A preferred concentration range for such a lipid component would be 50 to 200 μg/ml.

The formulation of the invention may also contain N-acetylcysteine as a mucolytic agent.

In one aspect the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art. In another aspect, components of the invention may be delivered to the eye as a concentrated gel or similar vehicle which form dissolvable inserts that are placed beneath the eyelids.

In a general aspect, the invention aims to provide a substitute for natural tears that does not have just a mucus binding and/or lubricating capability. In addition or alternatively, the invention would reproduce the viscosity and surface tension properties of natural tears by way of its possible formulations, as detailed above. The formulation of the invention is useful in the treatment of eye irritations for example, those caused by environmental conditions such as atmospheric pollution or use of visual display units. The formulation may also be used with contact lenses or other ophthalmic products.

FIGURES

The examples that follow are more clearly described with reference to the following figures:

FIG. 1A. Graph showing the relationship between shear rate ($s^{x1}$) and viscosity ($mPa.s^{-1}$) for whole tears.

Figure 1B:
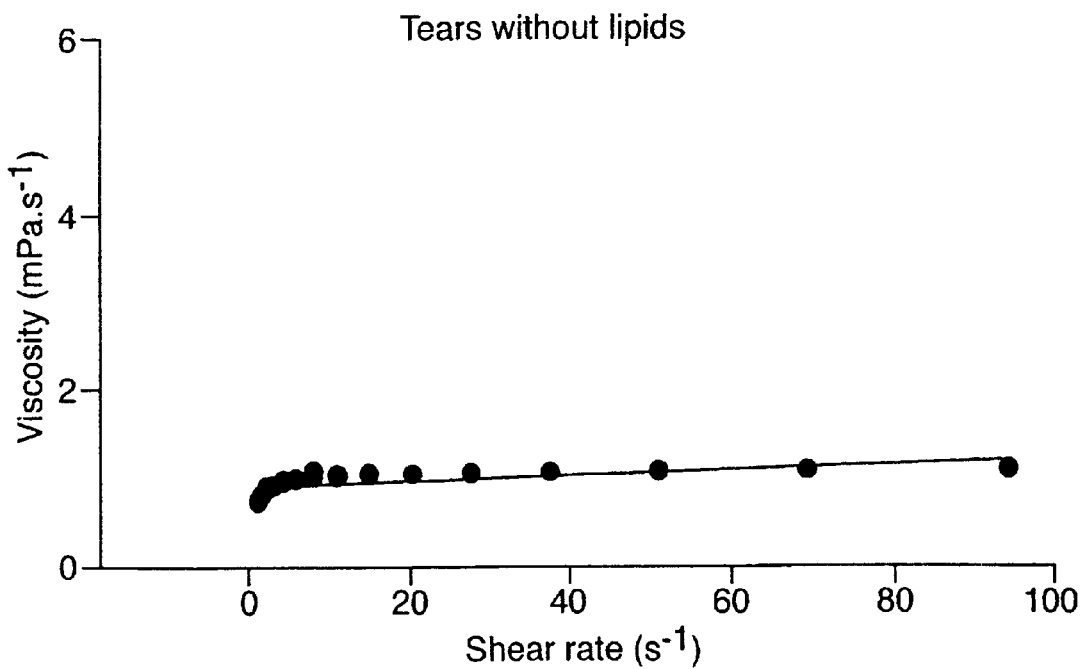

FIG. 1B. Graph showing the relationship between shear rate ($s^{-1}$) and viscosity ($mPa.s^{-1}$) for tears with lipids removed.

FIG. 2. Graph showing the relationship between shear rate ($s^{-1}$) and viscosity ($mPa.s^{-1}$) for lactoglobulin and combinations of lactoglobulin with tear lipids, phosphotidylcholine, sphingomyelin, cerebrosides, cholesterol, and gangliosides

Example 1

Effect of extraction of lipids from tears on physical properties, and effect of adding lipid back The inventors have examined the effects on tear surface tension of extracting lipids from pooled stimulated tears with hexane. Tears and an equal volume of hexane were mixed thoroughly; the tube was centrifuged to separate the phases, then the upper (hexane) phase was removed. Surface tension was determined by the method of Tiffany et al. (1989) on the lower phase, and found to be significantly higher (less surface-activity) than whole tears. The hexane phase was evaporated to dryness and the lipid-free extract added to it and mixed to reconstitute the whole tears. The surface tension of this was found to equal that of the original tears (Table 1).

TABLE 1

Surface tension of whole stimulated tears and the effect of lipid extraction

|  | ST (mean, SD) |
| --- | --- |
| Whole tears | 46.00 (0.52) |
| Tears after lipid extraction | 53.61 (0.19) |
| Reconstituted tears | 46.55 (0.30) |
| Saline after adding lipid back | 53.86 (0.31) |

Lipid extraction almost completely eliminated shear dependence of viscosity for stimulated tears (FIG. 1B), but it was fully regained on adding back the extracted lipid (FIG. 1A)

Example 2

Effects of adding back representatives of various classes of lipid on the physical properties The inventors have added back a series of different lipids to lipid-free tears (an equal amount each time); all improved the surface tension. These results cannot be directly compared with the effect of natural tear lipids since its concentration in tears is unknown, therefore an exactly equivalent amount of lipid has not been added. The greatest effect was seen with polar lipids, including phospholipids and sphingolipids. This was seen with both surface tension (Table 2) and viscosity.

TABLE 2

Surface tension of lipid-free tears (type, class) with model lipids

|  | ST (mean, SD) |
| --- | --- |
| Whole tears | 43.3 (0.33) |
| Lipid-free tears + Meibomian lipids | 48.7 (0.36) |
| Octadecyl stearate (wax ester) | 46.82 (0.31) |
| Cholesteryl stearate (sterol ester) | 47.13 (0.41) |
| Tristearin (triacyl glyceride) | 52.70 (0.29) |
| Stearic acid (free fatty acid) | 47.29 (0.23) |
| Dioleoyl phosphatidylcholine (phospholipid) | 42.40 (0.24) |
| Ceramide mixture | 45.76 (0.76) |
| Gangliosides (glycolipids) | 47.28 (1.05) |
| Sphingosine | 43.74 (0.25) |
| Galactosphingosine (glycolipid) | 42.20 (0.33) |

It should be noted that, although Meibomian lipids contain phospholipids, they are either of the wrong type or present at too low a level to restore full function. In two cases (dioleoyl-PC and galactosphingosine) the recovery appears even to exceed the original surface activity, but this may depend on the amount added, or, being significantly water-soluble, they may show the properties of the lipid itself rather than its combination with tear proteins. The value for tear surface tension differs from that in Table 1, but shows the variation possible between groups. Both values are within the normal range.

Example 3

State of lipids in tears

To determine whether the lipid exists free in solution (as a monomer/micelle equilibrium) or bound to proteins only, the inventors centrifuged tears in a micro-centrifuge tube filter. This uses a membrane with a nominal size-exclusion limit of 5 kDa, although in practice molecules up to about 15 kDa may pass; all the principal tear proteins should hence be retained, but the aqueous medium and any contained micellar lipids should pass through the filter. After 2 hours at 13000 rpm virtually all fluid had passed through. The residue was reconstituted in saline to the original volume, and surface tension was measured on the filtrate, the reconstituted tears, and reconstituted tears after extracted of lipid (Table 3).

TABLE 3

Surface tension of filtered tears

|  | ST (rnN/m) (mean, SD) |
| --- | --- |
| Tear filtrate | 61.72 (0.20) |
| Reconstituted tears (residue + saline) | 45.95 (0.33) |
| Reconstituted tears after lipid extraction | 51.39 (0.33) |

This clearly suggests that the active substances are largely unable to pass through the filter, and that the lipid is still extractable from the reconstituted residue, and presumably bound to protein.

Example 4

Attempts to identify the lipids extracted from the tears

The inventors have made a preliminary characterisation of the lipid extracted from tears by thin-layer chromatography (TLC) and gas-liquid chromatography (GLC), and by high-performance liquid chromatography (HPLC) on normal and reversed-phase columns. By simply injecting a sample of the extract into the GLC the inventors obtained a pattern of peaks which is substantially different from that obtained with Meibomian lipids from the same subject. However, many lipids, including polar lipids (whose effectiveness was indicated in Example 2 are involatile or partially or completely break down at the GLC running temperatures, so any peaks seen may be either breakdown products or from other inactive components. It is interesting that little correspondence is seen with the Meibomian trace, though.

Several TLC systems were used, optimised for separation of different parts of a lipid mixture. A general separation shows separation of Meibomian lipid into a series of classes, of which the wax esters and sterol esters predominate, although polar lipids can be seen near the origin. With a more polar developing solvent, the non-polar classes run much higher and the polar classes are more spread. Material extracted from tears is seen in this polar region.

Separation of the lipid extract was also performed by HPLC, on a reversed-phase column. A TSK-3000 size exclusion column has also been used for HPLC separation of the protein constituents of tears (Fullard, 1988).

Example 5

Experiments with individual model proteins and tear lipid extract or model lipids. Identification of the macromolecular constituents of tears which are involved in the physical properties The principal proteins of human tears are lysozyme, lactoferrin, secretory IgA (immunoglobulin A) and tear lipocalin. Samples of the first three (from non-tear sources) are commercially available, and the inventors have recently also used β-lactoglobulin as a model for tear lipocalin. Various combinations of these, with and without tear lipid extract or with other model lipids, have been used to measure surface tension (Table 4) and viscosity (FIG. 2). The concentrations of the tear proteins were always as reported for tears by Fullard (1988). Note that many results have been omitted from this table.

TABLE 4

Surface tension of model protein solutions with added lipids

|  | ST (mean, SD) |
| --- | --- |
| Lysozyme + lactoferrin + IgA | 55.76 (0.24) |
| Lysozyme + lactoferrin + IgA + tear lipids | 53.96 (0.26) |
| β-lactoglobulin + tear lipids | 46.44 (0.49) |

With surface tension, the conclusion is clear: no combination of proteins alone gives the same value as intact tears, and even with tear lipids a lipocalin must be present to give maximal surface activity. The conclusion is that tear surface tension is largely determined by some unspecified interaction between tear lipocalin and a class or classes of lipids found in aqueous tears.

The situation is rather different with viscosity, because of the difficulty of matching of the results of different runs. Shear-thinning behaviour is shown with several combinations of proteins and lipids, but most strongly (judged by greater values of high-shear viscosity, and by a more sharply-curved trace) when lipocalin is present, and, apart from tear lipid extract, the most effective model lipids were sphingomyelin and cerebrosides.

References

Flower DR (1996). The lipocalin protein family: structure and function. *Biochem J* 318: 1–14.

Fullard R J (1988). Identification of proteins in small tear volumes with and without size exclusion HPLC fractionation. *Curr Eye Res* 7: 163–179.

Glasgow B J, Abduragimov A R, Farahbakhsh Z T, Faull K Y, Hubbell W L (1995) Tear lipocalins bind a broad array of lipid ligands. *Curr Eye Res* 14: 363–372.

Gunstone F D, Herslöf, B G (1992). A Lipid Glossary. The Oily Press Ltd., Dundee.

Moore J C, Tiffany J M (1979). Human ocular mucus. Origins and preliminary characterisation. *Exp Eye Res* 29: 291–301.

Stuchell R N, Slomiany B L, Joswiak Z, Murty V L N, Slomiany A, Farris R L (1984) Lipid composition of human tears. *Invest Ophthalmol Vis Sci* 25: 320.

Tiffany J M Winter N Bliss G (1989). Tear film stability and tear surface tension. *Curr Eye Res* 8: 507–515.

Tiffany J M (1991). The viscosity of human tears. *Int Ophthalmol* 15: 371–376.

Tiffany J M, Pandit J C, Bron A J (1996). Soluble mucins and the physical properties of tears. *Invest Ophthalmol Vis Sci* 37: S845.

What is claimed is:

1. A formulation suitable for application to mammalian eyes which formulation comprises:

a pharmaceutically acceptable, substantially isotonic aqueous electrolyte buffered it a pH of 5 to 8.5, containing a lipid binding protein at a concentration of from 0.01 to 50 mg/mL;

and a polar lipid selected from phospholipids and glycolipids, at a concentration of from 1 µg/ml to 10 µg/ml, wherein the lipid and lipid binding protein are present as 4 soluble complex in the aqueous electrolyte.

2. A formulation as claimed in claim 1, in which at least one pharmaceutically acceptable preservative or bacteriostatic compound is present.

3. A formulation as claimed in claim 1 which shows shear-thinning.

4. A formulation as claimed in claim 1 which has a surface tension of less than 47 mN/m.

5. A product consisting of a vessel and contained therein a formulation according to claim 1, wherein the vessel is a single dose ampoule, or a multi-dose container with or without an extraction means for removal of preservative prior to delivery.

6. A formulation as claimed in claim 1 wherein the lipid binding protein is tear-specific prealbumin.

7. A formulation as claimed in claim 1 wherein the lipid binding protein is selected from the group consisting of lysozyme, lactoferrin, 1 gA, and β-lactoglobulin.

8. A formulation as claimed in claim 1 wherein the lipid binding protein is recombinant human tear-specific prealbumin.

9. A formulation as claimed in claim 1 wherein the formulation further comprises a mucolytic agent.

10. A formulation as claimed in claim 1 wherein the mucolytic agent is N-acetylcysteine.

11. A formulation as claimed in claim 2, wherein the preservative or bacteriostatic compound is selected from the group consisting of benzoalkonium chloride, disodium EDTA, and sodium perborate.

12. A formulation as claimed in claim 1 which has an osmotic pressure of 200 to 500 mOsmol/kg.

13. A formulation as claimed in claim 1, wherein the aqueous electrolyte is selected from the group consisting of Na, K, Ca, Mg, Cl, $HCO_3$, and combinations thereof.

14. A formulation suitable for application to mammalian eyes which formulation comprises:

pharmaceutically acceptable, substantially isotonic aqueous electrolyte buffered at a pH of 5 to 8.5, containing a tear-specific prealburnin at a concentration of from 0.01 to 50 mg/mL;

and a polar lipid selected from phospholipids and glycolipids, at a concentration of from 1 $\mu$/ml to 10 µg/ml.

15. A formulation suitable for application to mammalian eyes which formulation comprises:

a pharmaceutically acceptable, substantially isotonic aqueous electrolyte buffered at a pH of 5 to 8.5, containing a lipid binding protein at a concentration of from 0.01 to 50 mg/mL;

and a polar lipid, wherein the lipid and lipid binding protein are present as a soluble complex in the aqueous electrolyte.

16. A formulation as claimed in claim 15 wherein the polar lipid is selected from the group consisting of phospholipids, glycolipids, and sphingolipids.

17. A formulation as claimed in claim 16 wherein the polar lipid is at a concentration of from 1 µg/ml to 200 µg/ml.

* * * * *

UNITED STATES PATENT AND TRADEMARK OFFICE
CERTIFICATE OF CORRECTION

PATENT NO.     : 6,565,861 B1
DATED          : May 20, 2003
INVENTOR(S)    : John M. Tiffany et al.

It is certified that error appears in the above-identified patent and that said Letters Patent is hereby corrected as shown below:

Column 7,
Line 3, "µg/ml," should read -- mg/ml, --
Line 4, "4" should read -- a --
Line 21, "1 gA" should read -- IgA --

Column 8,
Line 10, "prealburnin" should read -- prealbumin --
Line 14, "µg/ml." should read -- mg/ml. --

Signed and Sealed this

Twenty-seventh Day of April, 2004

JON W. DUDAS
*Acting Director of the United States Patent and Trademark Office*